US006048720A

United States Patent [19]
Dalborg et al.

[11] Patent Number: 6,048,720
[45] Date of Patent: Apr. 11, 2000

[54] CONJUGATES OF A POLYPEPTIDE AND A BIOCOMPATIBLE POLYMER

[75] Inventors: Johanna Dalborg, Stockholm; Helena Sandberg, Bromma; Anna-Lisa Smeds, Sollentuna; Eva Åkerblom, Uppsala, all of Sweden

[73] Assignee: Pharmacia & Upjohn AB, Stockholm, Sweden

[21] Appl. No.: 09/029,672

[22] PCT Filed: Sep. 27, 1996

[86] PCT No.: PCT/SE96/01215

§ 371 Date: May 21, 1998

§ 102(e) Date: May 21, 1998

[87] PCT Pub. No.: WO97/11957

PCT Pub. Date: Apr. 3, 1997

[30] Foreign Application Priority Data

Sep. 29, 1995 [SE] Sweden .................................. 9503380

[51] Int. Cl.[7] .............................. C12N 9/50; A61K 35/14; A61K 38/16
[52] U.S. Cl. .......................... 435/219; 530/383; 530/815; 530/812; 530/813; 514/8; 514/834
[58] Field of Search ..................................... 530/383, 815, 530/829, 812, 813; 435/219; 514/8, 834

[56] References Cited

U.S. PATENT DOCUMENTS

| 4,904,584 | 2/1990 | Shaw ........................................ 435/69.4 |
| 4,970,300 | 11/1990 | Fulton et al. ............................ 530/383 |

FOREIGN PATENT DOCUMENTS

| 0197901 | 10/1986 | European Pat. Off. . |
| 3717210 | 12/1988 | Germany . |
| 59-172425 | 9/1984 | Japan . |
| WO9109122 | 6/1991 | WIPO . |
| WO9308838 | 5/1993 | WIPO . |
| WO9413322 | 6/1994 | WIPO . |
| WO9415625 | 7/1994 | WIPO . |
| WO9429370 | 12/1994 | WIPO . |

OTHER PUBLICATIONS

S. Zalipsky et al, *Poly(Ethylene Glycol) Chemistry, Bioctechnical and Biomedical* Applications, Plenum, New York (1992).
N.V. Katre, *Adv. Drug Deliv. Rev.*, (1993) 10:91–114.
Y. Inada et al, *Trends in Biotechnology*, (1995) 13:86–91.
G.E. Francis et al, *Stability of Protein Pharmaceuticals/Series: Pharmaceutical Biotechnology* (1992) 3:235–263.
S. Dreborg et al, *Crit. Rew. Therap. Drug Carr. Sys.*, (1990) 6(4):315–365.
M.S. Hershfield et al, *New Eng. J. Med.*, (1987)316:589–596.
J. Gitschier et al, *Nature*, (1984) 312:326–330.
W.I Wood et al, *Nature*, (1984) 312:330–337.
J.J. Toole, *Nature*, (1984) 312:342–347.
R.J. Kaufman et al, *J. Biol. Chem.*, (1988) 263(13):6352–62.
L.O. Anderson et al, *Proc. Natl. Acad. Sci.*, (1986) 83:2979–83.
P. Lind et al, *Eur. J. Biochem*, (1995) 232:19–27.
J.A. Koedam et al, Doctoral Thesis, ICG Printing, Dordrecht (1986) 74–90.
E.G.D. Tuddenham et al, *Br. J. Haematol.*, (1982) 52:259–267.
K.M. Brinkhous et al, *Proc. Natl. Acad. Sci.*, (1985) 82:8752–8756.
R.G. DiScipio et al, *Biochemistry*, (1977)16:698–705.
K. Nilsson et al, *Methods in Enzymology*, (1984)104:56–69.
A. Garman et al, *Febs Letters*, (1987) 223(2):361–365.
J.C. Jansson et al, *Protein Purification, Principles, High Resolution Methods and Applications*, VCH Publishers (1989) 274–285.
J.J. Morgenthaler et al, *Thromb. Haemostas.*, (1982) 47(2):124–127.
M. TeBooy et al, *J. Chrom.*, (1990)503:103–114.
M. Mikaelsson et al, *Blood*, (1983)62:1006–1015.
C. Fulcher et al, *Blood*, (1983)61:807–811.
D. Eaton et al, *Biochemistry* (1986)25:505–512.
F. Rotblat et al, *Biochemistry* (1985)24:2494–4300.

*Primary Examiner*—Karen Cochrane Carlson
*Assistant Examiner*—Holly Schnizer
*Attorney, Agent, or Firm*—Dinsmore & Shohl LLP

[57] ABSTRACT

Processes for improving the in vivo function of factor VIII by shielding exposed targets of the factor VIII comprise a) immobilizing the factor VIII by interaction with a group-specific adsorbent carrying ligands manufactured by organic-chemical synthesis, for preventing polymer coupling to reactive amino acids of the immobilized factor VIII, within or adjacent to interaction domains; b) activating a biocompatible polymer; c) conjugating the activated biocompatible polymer to external sites of the immobilized factor VIII; and thereafter d) eluting the conjugate from the adsorbent. Processes for administering factor VIII comprise subcutaneously, intramuscularly, intradermally or intravenously administering a conjugate of factor VIII and a biocompatible polymer, and methods for treatment of hemophilia A comprise subcutaneous, intramuscular, intradermal or intravenous administration of a conjugate of factor VIII and a biocompatible polymer.

20 Claims, 2 Drawing Sheets

CONJUGATES OF A POLYPEPTIDE AND A BIOCOMPATIBLE POLYMER

FIELD OF THE INVENTION

The present invention relates to a process for improving the in-vivo function of a polypeptide by shielding exposed targets of said polypeptide, by immobilizing the polypeptide to a group-specific adsorbent carrying ligands manufactured by organic-chemical synthesis, activating the biocompatible polymer, conjugating the thus activated biocompatible polymer to the immobilized polypeptide, and thereafter eluting the conjugate from the adsorbent. The present invention further relates to conjugates of a polypeptide and a biocompatible polymer obtainable by the present process, and use of said conjugates as medicaments. Specifically, the polypeptide is factor VIII, the von Willebrand factor or factor IX. The invention is particularly advantageous for conjugates where the polypeptide is factor VIII with a high specific activity using monomethoxy polyalkyleneoxide (mPEG) as the biocompatible polymer.

BACKGROUND OF THE INVENTION

It is well known, that the in-vitro stability and in-vivo half-life of polypeptides can be increased by covalent attachment of biocompatible polymers (in the following referred to as conjugation or modification). Modification of the polypeptide surface also has the advantage of decreasing the immunogenicity exhibited by the polypeptide.

Pegylation, i.e. coupling of various polyethyleneglycols (PEG) to a polypeptide, is a technique widely used for increasing the in-vitro stability and in-vivo half-life of e.g. proteins. In pegylation, many techniques have been proposed over the years. Reference is here made to Zalipsky, S. et al in Poly(Ethylene Glycol) Chemistry, Biotechnical and Biomedical Applications, Plenum, N.Y. (1992), and Katre N. V., Adv. Drug Deliv. Rev., 10 91–114 (1993).

For some polypeptides, a loss of activity or function has been recognized as a consequence of this conjugation, an effect that increases by degree of modification (Inada, Y. et al, Trends in Biotechnology, 13, 86–91 (1995)). Methods have been developed for making coupling more selective, to circumvent this problem. Site-directed mutagenesis for instance, has been applied for recombinant interleukin-2 (rIL-2). A specific target can be created by insertion of a cystein (Goodson, R. J. and Katre, N. V., Bio/Technology 8, 344–346 (1990); Katre 1993, see above). Such a route is not generally applicable for therapeutic proteins, since amino acid substitution may change the original characteristics of the molecule, and is therefore controversial. Alternatively, the polymer can be directed towards glycosylated sites of a protein, e.g. factor IX as disclosed in WO 94/29370 (Enzon). This involves, however, oxidation of the carbohydrate moieties which can be achieved by reacting the glycoprotein with sodium periodate or enzymatically by galactose oxidase. These conditions are often detrimental for the molecule. In this particular case, the glycosylated sites intended for conjugation were located at a factor IX peptide sequence which is removed during proteolytic activation in-vivo. Hence, the biocompatible polymer does not influence the function of the active polypeptide.

In WO 94/13322 (Farmitalia Carlo Erba) it is shown that pegylation can be carried out without impairing the function of certain sites essential for the function of the particular protein ("first substance"). This is achieved by protecting the sites by contacting the first substance with a second substance which specifically binds to the said sites. More particularly, the pegylation is carried out by immobilizing the particular protein on a resin with ligands having specific affinity to the said protein. Second substances are for instance complementary biological molecules. Examples of couples disclosed in WO 94/13322 are antibody (first substance)—corresponding antigen (second substance); specific inhibitor (first substance)—enzyme (second substance); growth factor (first substance)—corresponding receptor (second substance), or the reverse of each of these couples.

In a process intended for pharmaceutical production it is however advantageous if the use of substances of biological complexity can be kept at a minimum. This is primarily due to the strict requirements for documentation on biochemical homogeneity and safety for the use of said substances. Therefore, the use of affinity ligands produced by organic-chemical synthesis would be advantageous.

DE 3717210 relates to a process for modification of biopolymers, preferably charge-carrying biopolymers, by immobilizing the biopolymer on for instance an ion-exchange adsorbent, reacting the biopolymer with reagents, e.g. enzymes or other biochemical reagents, for obtaining a reaction product and subsequently desorbing the reaction product from the adsorbent. The reaction product is preferably a nucleic acid cleaved with a restriction enzyme. In DE 3717210 the adsorbed state of the biopolymer is utilized to better expose the biopolymer to reagents, thereby increasing the efficiency of the modification. There is no indication of shielding exposed targets nor a purpose of retaining activity of the biopolymer, that would come to advantage for a function of the biopolymer in-vivo. The invention of DE 3717210 is merely aimed at mapping properties of biomolecules, such as nucleic acids, changing the original character by actual processing or increasing the number of functional entities of the macromolecule, such as incorporation of radioactive isotopes.

Many proteins intended for therapeutic use have been conjugated, commonly by use of various pegylation techniques (Francis, G.E. et al, in Stability of Protein Pharmaceuticals/Series: Pharmaceutical Biotechnology 3, 235–263 (1992); Inada, Y. et al, Trends in Biotechnology, 13, 86–91 (1995)). Most examples concern intravenous administration. However, uptake after subcutaneous administration to plasma, lung, liver, and spleen of some mPEG-conjugated allergens has been disclosed and immunotherapy with mPEG-conjugated allergens given subcutaneously has proven to be effective (Dreborg, S. and Åkerblom, E. B., Crit. Rew. Therap. Drug Carr. Sys. 6(4), 315–365 (1990)). Also, intramuscular administration has been used in clinical trials of adenosine deaminase (Hershfield, M. S. et al, New Eng. J. Med. 316, 589–596 (1987). Pegylation has also been claimed, in a few cases, to be beneficial for the oral route. Thus, pegylation lation of IgG for oral administration has been disclosed in EP-A-0 614 373 to Mount Sinai School of Medicine. Pegylation of factor VIII and factor IX for oral administration has been disclosed in Sakuragawa et al, Acta Med. Biol., 34(3), 77–84 (1987) and in Japanese Patent Application No. 44509/83 to Nippon Chemifar Company.

Factor VIII is a protein which participates in the intrinsic blood coagulation. It is a cofactor in the reaction where the enzyme factor IXa in the presence of phospholipid and calcium ions converts the proenzyme factor X to the active form, factor Xa, ultimately leading to a fibrin clot. Human factor VIII is synthesized as a single-chain molecule of approximately 300 kDa and consists of the structural domains A1-A2-B-A3-C1-C2 (Gitschier et al., 1984, Nature 312, p. 326; Wood et al., 1984, Nature 312, p. 330; Vehar et al., 1984, Nature 312, p. 337; Toole et al., 1984, Nature, 312, p.342). The precursor product is processed into two polypeptide chains of 200 and 80 kDa in the Golgi and the two chains held together by metal ion(s) are expressed in the blood (Kaufman et al., 1988, J. Biol. Chem., 263, p. 6352; Andersson et al., 1986, Proc. Natl. Acad. Sci., 83, p. 2979). The B-domain of factor VIII seems to be dispensable as regards the factor VIII cofactor function while the A and C domains have several interaction sites for other macromolecules playing a role in the hemostasis (Sandberg et al., 1993, Thrombos. Haemostas., 69, p. 1204 and Lind et al., 1995, Eur. J. Biochem., 232, p. 19).

The von Willebrand factor (vWf) is a multifunctional polymeric plasma protein consisting of disulfide-linked subunits of about 240 kDa. The subunits form a heterogeneous population of multimers that have a range of molecular weights from c. 1 MDa to 20 MDa. The function of vWf in primary hemostasis is to promote platelet adhesion to the vessel wall in conditions of high shear rate. vWf also binds factor VIII tightly but noncovalently. In normal human plasma factor VIII and vWf circulate complexed to each other. vWf has an important stabilizing effect on the factor VIII molecule in that it protects the molecule from degradation by proteases (Koedam et al., 1987, Doctoral Thesis, ICG Printing, Dordrecht, 1986, p 83; Hamer et al., 1986, Haemostasis, 1987, 58, p. 223). The human in-vivo half-life of factor VIII is usually 10–15 hours. In vWf deficient patients the reduced levels of vWf are accompanied by reduced levels of factor VIII due to an impaired release and increased rate of degradation of factor VIII. Tuddenham et al., 1982, Br. J. Haematol., 52, p. 259 and Brinkhous et al., 1985, Proc. Natl. Acad. Sci., 82, p. 8752 showed that the presence of vWf has an important effect on the in-vivo survival of factor VIII. When factor VIII was infused in hemophilic dogs a half-life of 7–10 hours was obtained while the half-life was c. 1 hour after infusion in vWf deficient dogs (Brinkhous et al., see above).

Factor IX is the proenzyme of factor IXa described above. It is a serine protease and is one of the vitamin K dependent coagulation proteins. The molecular mass is about 55 kDa (DiScipio et al., 1977, Biochemistry, 16, p. 698). Factor IXa interacts specifically with other components participating in the factor X activation (In: Haemostasis and Thrombosis, 1994, vol. 1, third edition, ed. Bloom A. et al.)

It is evident from the above paragraphs, that factor VIII is a protein with several interaction sites, each responsible for a specific function. Therefore, it is difficult to modify factor VIII with fully retained biological function.

The pegylation technique has been applied previously to protein mixtures containing factor VIII. Thus, it has been disclosed in WO 94/15625 (Enzon) that pegylation of factor VIII using a carbamate (urethane) linkage at an undetermined modification degree resulting from a 100 fold molar excess of mPEG relative to factor VIII, can increase the in-vivo half-life in mice from 13 hours to 55 hours. Conventionally, the half-life in mice is considered to be about 1 hour. Thus, 13 hours is an unusually long half-life in mice. Furthermore, it must be taken into account, that with the extremely low purity of the starting factor VIII preparation (20–50 IU/mg protein), other proteins than factor VIII were predominant during the coupling reaction. One important protein usually present in factor VIII preparations of low purity is the von Willebrand factor, which has a stabilizing function for factor VIII and could also very well contribute to the protection of the corresponding functional site during the process of conjugation. After conjugation, mPEG can be located on any of the proteins present in the protein mixture of which factor VIII normally constitutes only a small portion. The pegylated protein mixture containing factor VIII was used for intravenous administration. A well defined starting material, however, is one of the essential factors constituting the controlled conditions required for pharmaceutical production.

Other polymers have also been used for conjugating factor VIII. Thus, it has been disclosed in U.S. Pat. No. 4,970,300, that dextran conjugation can be applied to prolong the half-life of factor VIII.

In most coupling techniques, the polymer reagent reacts with $\epsilon$-amino groups of lysine residues of the polypeptide. These are often spread all over the polypeptide surface, and may very well result in a conjugation adjacent to a functional site. As a consequence, by random coupling, the activity or function is often disturbed. It is our experience, that when applying such techniques to very pure preparations, such as a B domain-deleted recombinant factor VIII with coagulant activity, this activity is severely diminished already at a modification degree of about 5 mPEG/factor VIII molecule.

SUMMARY OF THE INVENTION

The inventors of the present invention have found that the specific activity of conjugated polypeptides can be retained to a high degree, purely by immobilizing the polypeptide on a group-specific adsorbent prior to the coupling reaction, which is followed by desorption of the conjugate by conventional techniques. This is quite surprising since previously it has been considered essential to use adsorbents with specific binding properties with respect to the polypeptide at issue to achieve a protection of certain domains, important for the biological functions.

The benefit of modifying biocompatible polymers often depends on the degree of modification. Thus, a high degree of modification, i.e. a high number of biocompatible polymers per polypeptide molecule, is usually required for an efficient protection against proteolytic activity. With the aid of the present invention, in which the biocompatible polymers are introduced more selectively, the specific activity has been better retained. Thus, the inventors of the present invention have found that factor VIII can be efficiently protected against degradation in an in-vitro environment shown to have a degrading effect on this molecule. This effect can be accomplished at a modification degree of only 4–5 mPEG/factor VIII.

The use of group-specific adsorbents according to the present invention is more economically favorable compared to the adsorbents disclosed in the prior art. The use of group-specific adsorbents will also facilitate registration of the conjugates as therapeutic agents.

The present process makes it possible to improve the in-vivo function of polypeptides, especially by improving the pharmacokinetic function including the bioavailability, and by reducing the immunogenicity exhibited by the polypeptides.

Thus, the present invention relates to a process for improving the in-vivo function of a polypeptide by shielding exposed targets of said polypeptide, by a) immobilizing the polypeptide by interaction with a group-specific adsorbent carrying ligands manufactured by organic-chemical synthesis;

b) activating the biocompatible polymer;

c) conjugating the activated biocompatible polymer to the immobilized polypeptide; and thereafter d) eluting the conjugate from the adsorbent.

DETAILED DESCRIPTION OF THE INVENTION

In the present invention, the term interaction site relates to various sites essential for the biological function of the particular polypeptide.

In the present invention, the term exposed targets relate to external sites on the polypeptide at issue liable to unwanted reactions in-vivo. Examples of exposed targets include antigenic epitopes and sites for proteolytic cleavage. Certain sites for proteolytic cleavage are though referred to as interaction sites.

The present invention makes it possible, to a hitherto unattainable extent, to reduce the influence of unwanted reactions in-vivo, e.g. proteolytic cleavage and possibly aggregation, while at the same time leaving the interaction sites fundamental to the biological function of the polypeptide, unaffected. This has been disclosed in the application of mPEG conjugation of (recombinant) factor VIII. More specifically, by immobilizing the polypeptide by interaction with a group-specific adsorbent carrying ligands manufactured by organic-chemical synthesis, the interaction sites on the polypeptide are excluded from conjugation to the biocompatible polymer. Furthermore, by conjugating the activated biocompatible polymer to the polypeptide at the desired, external sites, the exposed targets are concealed from the action of e.g. proteases.

In the present application, polypeptides refer to proteins and oligopeptides with at least 20 amino acids in the chain. The number of amino acids of the polypeptide produced according to the present invention suitably lies in the range of from 30 up to 4,500 amino acids, and preferably in the range of from 40 up to 3,000 amino acids. The polypeptides can be of mammalian, more specifically human, origin or produced by recombinant DNA techniques. Polypeptides which can be conjugated according to the present invention include polypeptides exhibiting coagulant activity or having a supporting function for coagulation. The polypeptides can be full-length, i.e. the sequence of amino acids is identical to the corresponding sequence found in mammals in general, and in human beings in particular. The polypeptides can also be deletion derivatives of the full-length polypeptides, where one or more amino acid is missing. The polypeptide is suitably coagulation factor VIII, the von Willebrand factor (vWf) or a combination thereof, or coagulation factor IX, and preferably coagulation factor VIII.

Full-length factor VIII present in human plasma has a molecular mass of about 300 kDa. Factor VIII concentrates derived from human plasma contain several fragmented fully active factor VIII forms as described by Andersson et al (see above). The smallest active form has a molecular mass of about 170 kDa and consists of two chains of about 90 kDa and about 80 kDa held together by metal ion(s). Reference is here made to EP-A-0 197 901 to Pharmacia & Upjohn AB. The biologically active factor VIII produced according to the present invention, therefore, suitably has a molecular mass in the range of from about 170 kDa up to about 300 kDa.

Pharmacia AB of Stockholm, Sweden, has developed a recombinant factor VIII product which corresponds to the 170 kDa plasma factor VIII form in therapeutic factor VIII concentrates. The truncated recombinant factor VIII molecule is termed r-VIII SQ and is produced by Chinese Hamster Ovary (CHO) cells in a cell culture process in serum-free medium. The specific activity of r-VIII SQ is about 15,000 IU VIII:C per mg of total protein. The structure and biochemistry of r-VIII SQ have been described in WO-A-91/09122 assigned to Pharmacia AB.

In the present invention, factor VIII can be either plasma factor VIII or recombinant factor VIII. When factor VIII is recombinant it can be full-length factor VIII, or preferably, a deletion derivative of full-length factor VIII having coagulant activity. More preferably, the deletion derivative is recombinant factor VIII SQ (r-VIII SQ). In this context, a deletion derivative is defined as a coagulation factor VIII, in which the whole or a part of the B domain is missing while the coagulant activity is maintained. The remaining domains are suitably linked by an amino acid linker. Examples of various linker constructions are given in P. Lind et al, Eur. J. Biochem., vol. 232 (1995) pp. 19–27.

The present invention can be used advantageously to selectively introduce biocompatible polymers in a wide variety of factor VIII products. Thus, the present invention can be used to further stabilize plasma factor VIII in-vivo, which is already stabilized by association with its carrier protein, the von Willebrand factor (vWf).

It is advantageous that the final product is well defined. Therefore, the specific factor VIII activity in the coupling procedure of the present invention should be at least about 1,000 IU/mg of total protein, and suitably at least 2,000 IU/mg of total protein. The specific factor VIII activity lies preferably in the range of from 5,000 up to 20,000 IU/mg of total protein, and more preferably in the range of from 10,000 up to 17,000 IU/mg of total protein.

The factor VIII activity in the coupling procedure can be at least about 1,000 IU/ml, and suitably at least 2,000 IU/ml. The factor VIII activity lies preferably in the range of from 5,000 up to 50,000 IU/ml, and more preferably from 20,000 up to 40,000 IU/ml.

The biocompatible polymer of the present invention can be selected from the group consisting of homopolymers, copolymers or block copolymers of monoalkyl-capped polyalkyleneoxides. The biocompatible polymers can be straight or branched. The monoalkyl-capped polyalkyleneoxide is suitably selected from the group consisting of polyethyleneglycol homopolymers and polypropyleneglycol homopolymers. The biocompatible polymer is preferably a polyethyleneglycol (PEG) homoplymer. The molecular weight of the PEG can be in the range of from about 300 up to 20,000, suitably in the range of from 1,500 up to 10,000, and preferably in the range of from 3,000 up to 5,000.

The biocompatible polymer should be end-capped at one end to avoid cross derivatization. Examples of groups suitable for this purpose are straight or branched lower alkoxy groups, preferably the monomethoxy group. A particularly preferred biocompatible polymer in the present invention is monomethoxy polyethyleneglycol (mPEG).

Other biocompatible polymers are also conceivable, e.g. dextran, polyvinylpyrrolidone and DL amino acids.

The biocompatible polymer must be activated prior to the coupling reaction, to make possible the formation of covalent bonds. For this purpose, the end of the biocompatible polymer facing the polypeptide should have attached a hydroxyl group being susceptible to activation. There are several ways of activating the biocompatible polymer depending on the amino acid selected for covalent binding. Suitable mPEG derivatives for coupling to amino groups are mPEG succinimidyl succinate, mPEG succinimidyl succinamide, mPEG succinimidyl propionate, succinimidyl carbonate of mPEG, succinimidyl ester of carboxymethylated mPEG, mPEG-oxycarbonylimidazole, mPEG nitrophenyl carbonates, mPEG trichlorophenyl carbonate, mPEG tresylate (the latter disclosed by Nilsson K., Mosbach K., Methods in Enzymology, Vol 104, pp 56–69 (1984)), (all the mentioned reagents marketed by Shearwater Polymers, Inc., Huntsville, Ala., USA), mPEG maleic anhydride and mPEG methylmaleic anhydride (Garman A., Kalindjian S. B., FEB Vol 223: 2, pp 361–365), and mixed anhydrides of mPEG succinate, mPEG acetic acid or mPEG propionic acid, respectively (Dreborg S. and Akerblom E., see above).

Cysteine residues can be conjugated with mPEG maleimide, mPEG vinylsulfone and mPEG-orthopyridyldisulfide (marketed by Shearwater Polymers, Inc., Huntsville, Ala., USA). Suitable reagents in the case of conjugation of the guanidino group of arginine is mPEG derivatives of phenylglyoxal (Zalipski see above).

Carbohydrates must first be oxidized so that aldehyde groups are present and then they can be conjugated with mPEG hydrazide (Zalipski see above).

The coupling procedure is performed at a pH suitable for the amino acid to be conjugated. Consideration must also be given to the pH suitable for the polypeptide at large, as well as the pH-dependency of the reactivity of the biocompatible polymer. Normally, therefore, the pH for coupling lies in the range of from about 7 up to about 8, the lower limit being set to avoid an extended coupling procedure and the upper limit to provide mild conditions for the polypeptide. The above pH range is suitable in conjugation involving lysines. Therefore, in the examples of the present application, we have conjugated a substance having FVIII activity under such mild conditions. pH values outside this range may also be suitable in certain cases. Thus, conjugation involving cysteins are suitably performed at a pH below about 7, whereas arginins are suitably conjugated at a pH in the range of from about 5.5 up to about 9.3.

The coupling procedure should be performed at a temperature above 0° C., suitably in the range of from about 5 up to about 40° C., and preferably in the range of from 10 up to 30° C. Again consideration must be given to a temperature suitable to the polypeptide at large, as well as the influence of the temperature on the reactivity of the biocompatible polymer. In the examples of the present application, all coupling steps were performed at room temperature.

The adsorbent used in the present invention is group-specific in relation to the polypeptide to be immobilized. Group-specific adsorbents have affinity to several polypeptides. Furthermore, they often bind less strongly and elution can be performed under milder conditions than with mono-specific adsorbents, the latter binding to a single or a very small number of polypeptides. Examples of suitable group-specific adsorbents are given in Jansson, J.-C. et al, Protein Purification, Principles, High Resolution Methods, and Applications, VCH Publishers, pp. 274–285 (1989), which is hereby incorporated by reference. The adsorbent of the present invention is furthermore characterized by carrying ligands manufactured by organic-chemical synthesis. Examples of adsorbents meeting these criteria are chromatography resins generally useful for the adsorption of proteins, e.g. biocompatible matrices to which ligands such as anionic and cationic exchange groups, sulfhydryl groups, immobilized metal affinity chromatography (IMAC) groups, straight or branched, saturated or unsaturated hydrocarbon chains and aromatic groups, have been coupled. Useful are also mixed-function ligands, for example with both ionic and hydrophobic parts, such as aminoalkyl or dimethylaminopropyl carbamylpentyl. These two ligands have been reported to be useful for the purification of plasma derived factor VIII, disclosed by Morgenthaler et al, Thromb. Haemostas. 47(2), 124 ff. (1982) and Te Booy, M. P. W. M., et al, J. Chrom. 503, 103–114 (1990), respectively. A preferred example of an aminoalkyl is aminohexyl. Ligands of higher complexity could also be used, such as peptides or phospholipids, manufactured by organic-chemical synthesis. For those skilled in the art, the group affinity ligands being manufactured by organic-chemical synthesis includes a large variety of substances. Thus, reactive triazine-based textile dyes have shown useful as adsorbents for several enzymes, like kinases and hydrogenases. Also, sugar derivatives, nucleotides and peptides, and analogues thereof and manufactured by organic-chemical synthesis are useful (Dechow, F. J., Separation and purification techniques in biotechnology, Noyes Publications, Park Ridge, N.J., USA, p. 440–443 (1989)).

Ligands suitable for use in the present invention are further anionic exchange groups, preferably strong, like quaternary aminoethyl (QAE), trimethylaminoethyl (TMAE) or quaternary aminomethyl (Q), more preferably quaternary aminomethyl (Q). The ligands can furthermore be coupled tightly to the matrix, or with a spacer, like alkylamine, hexylamine, diaminodipropylamine, ethylaminesuccinamide (Persson & Lagerström, in Packings and stationary phases in chromatographic techniques, Unger, K. K., ed., Marcel Dekker Inc. 1990, p. 754), or with a branched tentacle to which the ligands are attached (a suitable example is Fractogel™ EMD, produced by Merck of Germany).

After the said coupling procedure, the conjugated polypeptide is eluted by conventional techniques. In this context it is essential that physico-chemical conditions are considered to avoid degradation of the conjugated polypeptides. Thus, if the coupling route involves a conjugating bond labile within a certain pH range, this should be avoided.

In the coupling procedure, when the polypeptide is immobilized on the adsorbent, the polypeptide can be contacted with a soluble blocking agent, with the purpose of excluding additional sites from conjugation. Such a blocking agent should be manufactured by organic-chemical synthesis, and in addition be conjugated to any of the above-identified ligands bound to a polymer selected e.g. from monoalkyl-capped polyalkyleneoxides, copolymers or block copolymers of polyalkyleneoxides, polyethyleneglycol homopolymers or polypropyleneglycol homopolymers. The blocking agent can also carry entities having specific affinity for the polypeptide.

After the elution, the contacted soluble blocking agent is desorbed by applying suitable chemical conditions. For example if the blocking agent was adsorbed by hydrophobic interaction, it could be desorbed by decreasing the ionic strength, or simply by decreasing the temperature. The soluble blocking agent is thereafter separated from the conjugate by gel-permeation chromatography under conventional conditions.

The matrix of the adsorbent in the present invention, can be any commercial resin known to be compatible with biological molecules. Thus, the matrix can be selected from various strongly hydrophilic matrices e.g. agarose matrices such as a wide variety of Sepharose™ matrices sold by Pharmacia Biotech of Uppsala, Sweden, organic polymer matrices such as TSK-GEL:s sold by Tosoh Corp. of Tokyo, Japan, or highly porous organic polymer matrices sold by Per Septive Biosystems of Boston, USA. Membrane matrices are also suitable, e.g. Sartobind™ sold by Sartorius of Germany and MemSep™ sold by Millipore of USA. The matrix is preferably an agarose matrix. Suitable agarose matrices in the present invention are, apart from Sepharose™, Minileak™ sold by Kem-En-Tec A/S of Copenhagen, Denmark and Bio-Gel A sold by Bio-Rad, of Brussels, Belgium. Preferably, the matrix is cross-linked allowing for a fast flow (FF) and thereby high production capacity. More preferably, chromatography of the present invention is carried out on a Q Sepharose™ FF gel. Furthermore, resins composed of copolymers of oligoethyleneglycol, glycidyl methacrylate and pentaerythroldimethacrylate, like Fractogel™ (marketed by Merck of Germany), cellulose and porous glass can also be used to advantage.

The conjugates of a polypeptide and a biocompatible polymer obtainable by the present process are new. With the present process, the polypeptide activity after the conjugation can be retained to at least 30% of the activity prior to said conjugation, suitably at least 50% and preferably at least 70% of the activity prior to said conjugation.

The conjugates of a polypeptide and a biocompatible polymer obtainable by the present process can be used as medicaments. Especially, conjugates of factor VIII, the von Willebrand factor or a combination thereof, or factor IX, and a biocompatible polymer produced according to the present process can be used as a medicament. It is especially advantageous to use a conjugate of factor VIII and a biocompatible polymer, where the degree of conjugation lies in the range of from 1 up to 15 monoalkyl-capped PEG/factor VIII molecule, suitably in the range of from 2 up to 10 monoalkyl-capped PEG/factor VIII molecule, preferably in the range of from 3 up to 7 monoalkyl-capped PEG/factor VIII molecule. In this context, the conjugated factor VIII is suitably produced by recombinant DNA technique, preferably a recombinant deletion derivative of full-length factor VIII having coagulant activity, and more preferably deletion derivative recombinant factor VIII SQ (r-VIII SQ).

The conjugated polypeptides of the present invention are suitably used for subcutaneous, intramuscular, intradermal or intravenous administration. Especially, conjugated factor VIII can be used for the manufacture of a medicament for treatment of hemophilia A, and in particular for subcutaneous, intramuscular, intradermal or intravenous administration of such a medicament. Furthermore, conjugated vWf can be used for the manufacture of a medicament for treatment of the von Willebrand disease, and in particular for subcutaneous, intramuscular, intradermal or intravenous administration of such a medicament. Factor VIII and the von Willebrand factor, both of which have been conjugated according to the present process, can also be used in combination. Also, conjugated factor IX can be used for the manufacture of a medicament for treatment of hemophilia B, and in particular for subcutaneous, intramuscular, intradermal or intravenous administration of such a medicament.

The present invention further relates to a method for treatment of hemophilia A by subcutaneous, intramuscular, intradermal or intravenous administration of a conjugate of factor VIII and a biocompatible polymer produced according to the present process.

EXAMPLES

The following Examples are provided for purposes of illustration only and are not to be construed as in any way limiting the scope of the present invention, which is defined by the appended claims.

Example 1

Preparation of Recombinant Factor VIII

The production of recombinant factor VIII SQ (r-VIII SQ) was essentially performed as described in patent WO-A-9109122, example 1–3. A DHFR deficient CHO cell line (DG44N.Y.) was electroporated with an expression vector containing the r-VIII SQ gene and an expression vector containing the dihydrofolate-reductase gene. Following selection on selective media surviving colonies were amplified through growth in stepwise increasing amounts of methotrexate. Supernatant from the resulting colonies were individually screened for factor VIII activity. A production clone was chosen and this was subsequently adapted to serum free suspension growth in a defined medium and finally a large scale cell cultivation process was developed. Supernatant is collected after certain time periods and further purified as described below.

The conditioned medium was clarified by filtration, pH was adjusted, and then the filtrate was loaded onto a S Sepharose™ FF column (column volume 3 l). After washing, factor VIII was eluted with a salt buffer containing 5 mM $CaCl_2$ and 0.02% Triton™ X-100. This cationic exchange chromatography step was performed at 2–8° C. The eluate from the S Sepharose™ FF step (S-eluate) was frozen until further purification.

700 ml of the S-eluate was thawed and the temperature adjusted to room temperature. Virus inactivation was performed by incubation for 30 min with tri-n-butyl phosphate (TNBP) and Triton™ X-100 at a final concentration of 0.3% (v/v) and 1.0% (v/v), respectively. A monoclonal antibody (mAb) immunoaffinity column with a volume of 260 ml was equilibrated with an S-eluate buffer containing the corresponding amounts of virus inactivation chemicals. The factor VIII solution was then loaded onto the mAb column, which was subsequently washed. Elution was performed with a buffer containing 50% ethylene glycol.

A Q Sepharose™ column was preequilibrated at a high concentration of sodium chloride, and then equilibrated with a buffer of the same composition as the immunoaffinity column was eluted with. The mAb-eluate was loaded, and the column was then washed with equilibration buffer followed by a washing buffer of physiological ionic strength. The column was eluted by raising the sodium chloride concentration to 0.6 M. No detergent was used for the washing and elution of the Q-column. A Butyl Sepharose™ 4 FF column was equilibrated with a buffer containing 50 mM histidine, 1.4 M $NH_4Ac$, 50 mM $CaCl_2$, and 0.02% Tween™ 80, pH 6.8. $NH_4Ac$ was added to the Q-eluate to a final concentration of 1.0 M and Tween™ 80 to 0.02%. This solution was loaded onto the butyl-gel column at a linear flow rate of 60 cm/h. The column was then washed by 5 column volumes of equilibration buffer and then eluted at a linear flow rate of 35 cm/h with a buffer containing 50 mM histidine, 0.5 M $NH_4Ac$, 50 mM $CaCl_2$ and 0.02% Tween™ 80, pH 6.8. The purity of this preparation was very high, giving a specific activity of 12,000–17,000 IU/mg protein.

Analysis

In Examples 1–8, the factor VIII activity was analyzed with a chromogenic assay (Chromogenix AB of Mölndal, Sweden) unless otherwise stated. The amount of factor VIII was determined spectrophotometrically at A280 and by amino acid analysis. The amount of mPEG coupled to the polypeptide was measured with a proton NMR method (Dreborg, S. and Åkerblom, E. B., Crit. Rew. Therap. Drug Carr. Sys. 6(4), 315–365 (1990)).

Example 2

Comparative Example

Factor VIII Conjugated with a Mixed Anhydride of mPEG Succinate

The buffer composition of the HIC eluate, prepared according to Example 1, was exchanged by gel permeation chromatography performed on a Superose 12 column (marketed by Pharmacia Biotech of Uppsala, Sweden), previously equilibrated with a buffer of the following composition: 0.25 M hepes, 4 mM $CaCl_2$, pH 7.8. To aliquots of the r-VIII SQ solution were added a 35, 60 and 100 fold molar excess (based on rVIII) of a mixed anhydride of mPEG succinate (MW 3,000). The mixtures were allowed to react for 1.5 hours on a rotating device in room temperature. To remove the excess of mPEG succinic acid and to separate the heterogeneous population of conjugated rVIII according to size, gel permeation chromatography was performed, now using a Superose 6 column (marketed by Pharmacia Biotech of Uppsala, Sweden). From each coupling reaction the fractions corresponding to the first and second half of the protein peak were analyzed separately (denoted pool 1 and pool 2 in Table I). Table I presents the results of conjugating r-VIII SQ with the mixed anhydride of mPEG succinate.

Example 3

Factor VIII Adsorbed on a Q Sepharose™ FF Gel During Coupling with a Mixed Anhydride of mPEG Succinate Reactive lysines surrounded by negative charges on the factor VIII molecule were protected from mPEG conjugation by adsorption of the factor VIII on an anionic exchange gel. A column packed with Q Sepharose™ FF (marketed by Pharmacia Biotech of Uppsala, Sweden), equilibrated with a buffer of the following composition: 50 mM L-histidine, 0.15 M NaCl, 4 mM $CaCl_2$, pH 6.5, was used to adsorb factor VIII. A HIC eluate prepared according to Example 1 was loaded onto the column. In order to get appropriate conditions for mPEG coupling, the column was washed with a buffer containing 0.25 M hepes, 4 mM $CaCl_2$, pH 7.8 before the addition of the mPEG. The gel was transferred to a reaction vessel, a mixed anhydride of mPEG succinate (MW 3,000) was added to the slurry at an amount corresponding to the molar excess relative to factor VIII as indicated in Table II. The reaction was incubated under rotation for 1.5 hours. The column was then repacked and the conjugated rVIII was eluted with a buffer of 50 mM L-histidine, 0.6 M NaCl, 4 mM $CaCl_2$, pH 6.8. Four preparations were made, at a constant amount r-VIII SQ loaded per amount of gel. All steps were performed at room temperature. Table II presents the results from the conjugated r-VIII SQ adsorbed on a Q Sepharose™ FF gel.

TABLE I

|  | r-VIII SQ (mg) | Amount added mPEG (molar excess) | Degree of modification (mPEG/rVIII) | Spec. activity (IU/mg) | Spec. act (% of native r-VIII SQ) |
|---|---|---|---|---|---|
| Native r-VIII SQ | — | 0 | 0 | 15,000 | 100 |
| 35*mPEG pool 1 | 1.2 | 35 | 2.5 | 4,200 | 28 |
| 35*mPEG pool 2 | 1.2 | 35 | 1.2 | 6,800 | 45 |
| 60*mPEG pool 1 | 1.6 | 60 | 2.4 | 2,000 | 13 |
| 60*mPEG pool 2 | 1.6 | 60 | na | 4,800 | 32 |
| 100*mPEG pool 1 | 1.1 | 100 | 4.8 | 1,300 | 9 |
| 100*mPEG pool 2 | 1.1 | 100 | 3.8 | 2,700 | 18 |

As is evident from Table I, the specific activity of rVIII was reduced dramatically even at this low degree of conjugation.

TABLE II

|  | r-VIII SQ (mg) | Amount added mPEG (molar excess) | Degree of modification (mPEG/rVIII) | Spec. act. (IU/mg) | Spec. act (% of native r-VIII SQ) |
|---|---|---|---|---|---|
| Native r-VIII SQ | — | 0 | 0 | 15,000 | 100 |
| Preparation 1 | 1.9 | 300 | 3.9 | 8,400 | 56 |
| Preparation 2 | 1.9 | 370 | 4.4 | 7,800 | 52 |
| Preparation 3 | 1.9 | 430 | 5.6 | 6,800 | 45 |
| Preparation 4 | 1.9 | 530 | 9.5 | 2,800 | 19 |

As is evident from Table II, the specific activity of the conjugated r-VIII SQ is retained to a significantly higher degree compared to the r-VIII SQ conjugated in Example 2.

Example 4

FVII Adsorbed on a Q Sepharose™ FF Gel During Coupling with mPEG Tresylate

In this example all steps of adsorption, coupling and elution of r-VIII SQ on Q Sepharose™ FF gel were performed as in Example 3. mPEG tresylate (MW 5,000) was used to conjugate factor VIII. Table III presents the results from conjugated r-VIII SQ adsorbed on a Q Sepharose™ FF gel with mPEG tresylate according to the invention.

TABLE III

| | r-VIII SQ (mg) | Amount added mPEG (molar excess) | Degree of modification (mPEG/rVIII) | Spec. act. (IU/mg) | Spec. act. (% native r-VIII SQ) |
|---|---|---|---|---|---|
| Native r-VIII SQ | — | 0 | 0 | 15,000 | 100 |
| Preparation 1 | 1.8 | 300 | 2.2 | 9,600 | 64 |
| Preparation 2 | 1.8 | 400 | na | 8,300 | 55 |
| Preparation 3 | 1.8 | 500 | 5.8 | 3,400 | 23 |

The specific activity in this case was slightly lower than in Example 3, probably due to the higher molecular weight of mPEG.

Example 5

Factor VIII Adsorbed on a Tentacle Anionic Exchange Gel During Coupling with a Mixed Anhydride of mPEG Succinate A column packed with Fractogel™ EMD TMAE 650 (marketed by Merck), was used to adsorb r-VIII SQ. All steps were performed as in Example 3. Table IV presents the results from conjugation of r-VIII SQ adsorbed on a tentacle anionic exchange gel with a mixed anhydride of mPEG succinate according to the invention.

TABLE IV

| | r-VIII SQ (mg) | Amount added mPEG (molar excess) | Degree of modification (mPEG/rVIII) | Spec. act. (IU/mg) | Spec. act. (% native r-VIII SQ) |
|---|---|---|---|---|---|
| Native r-VIII SQ | — | 0 | 0 | 15,000 | 100 |
| Preparation 1 | 2.0 | 300 | na | na | |
| Preparation 2 | 2.0 | 500 | na | 2,100 | 14 |

Example 6

Thrombin Activation of mPEG Conjugated Factor VIII

Figure 1:
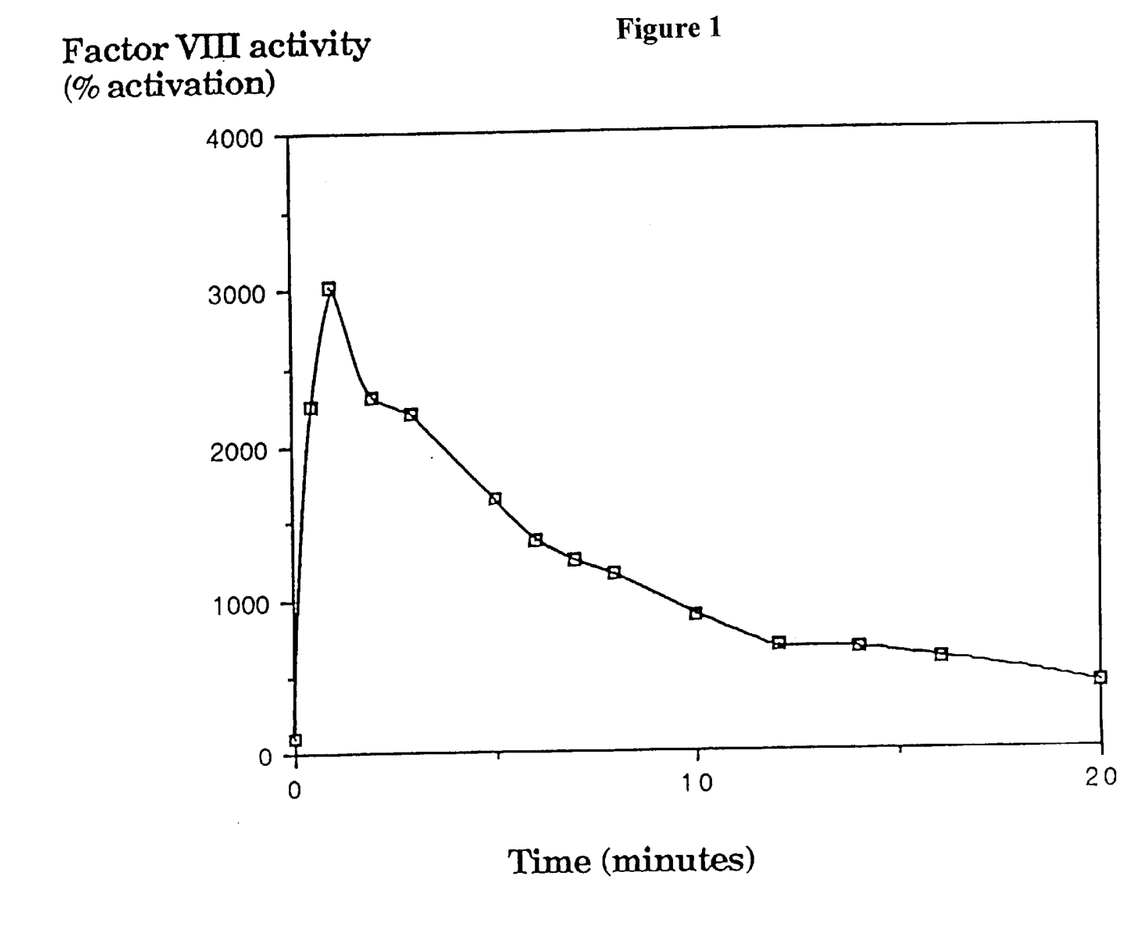
FIG. 1 sets forth the Factor VIII activity, as percent activation, as a function of time as obtain in the procedure described in Example 6.

Thrombin activation of conjugated r-VIII SQ was tested in an in-vitro assay well known to those skilled in the art. A sample prepared according to Example 3, resulting in a derivatization degree of 4 mPEG/r-VIII SQ, was assayed. The conjugated r-VIII SQ could be activated by human thrombin in a dose dependent manner. Inactivation was subsequently followed. In FIG. 1, the curve of activity changes obtained is shown when 1 NIH unit of thrombin per 1 unit of conjugated r-VIII SQ was added. A one-stage clotting method performed essentially according to Mikaelsson et al., 1983, Blood 62, p. 1006, was used for immediate assay of samples from the reaction mixture. A thirty-fold activation was obtained within one minute, which was followed by inactivation. The activation-inactivation patterns obtained with thrombin were in agreement with previously reported studies on the factor VIII-thrombin interaction (Fulcher et al., 1983, Blood, 61, p. 807, Andersson et al., 1986, Proc. Natl. Acad. Sci., 83, p. 2979, Eaton et al., 1986, Biochemistry, 25, p. 505, Rotblat et al., 1985, Biochemistry, 24, p. 4294).

Example 7

Stability Tests of mPEGylated Factor VIII in an Extract of Porcine Tissue

To evaluate the influence of the mPEG conjugation on the stability of factor VIII in a solution representative of the subcutaneous environment, an in-vitro test using extract of porcine tissue was undertaken. Two preparations of mPEG conjugated factor VIII were produced as described in Example 3 and incubated in the extract and aliquots were analyzed at 0, 2, 4, 6 and 24 hours for coagulant activity using a chromogenic assay. During the first 6 hours the degree of conjugation correlated to the remaining activity.

TABLE V

| | Remaining activity (%) 0 h | Remaining activity (%) 2 h | Remaining activity (%) 4 h | Remaining activity (%) 6 h | Remaining activity (%) 24 h |
|---|---|---|---|---|---|
| Native r-VIII SQ (control) | 100 | 45 | 13 | 6 | 0 |
| 4.4 mPEG/rVIII | 100 | 96 | 93 | 78 | 32 |

TABLE V-continued

|  | Remaining activity (%) 0 h | Remaining activity (%) 2 h | Remaining activity (%) 4 h | Remaining activity (%) 6 h | Remaining activity (%) 24 h |
|---|---|---|---|---|---|
| 9.5 mPEG/rVIII | 100 | 100 | 107 | 102 | 47 |

Figure 2:
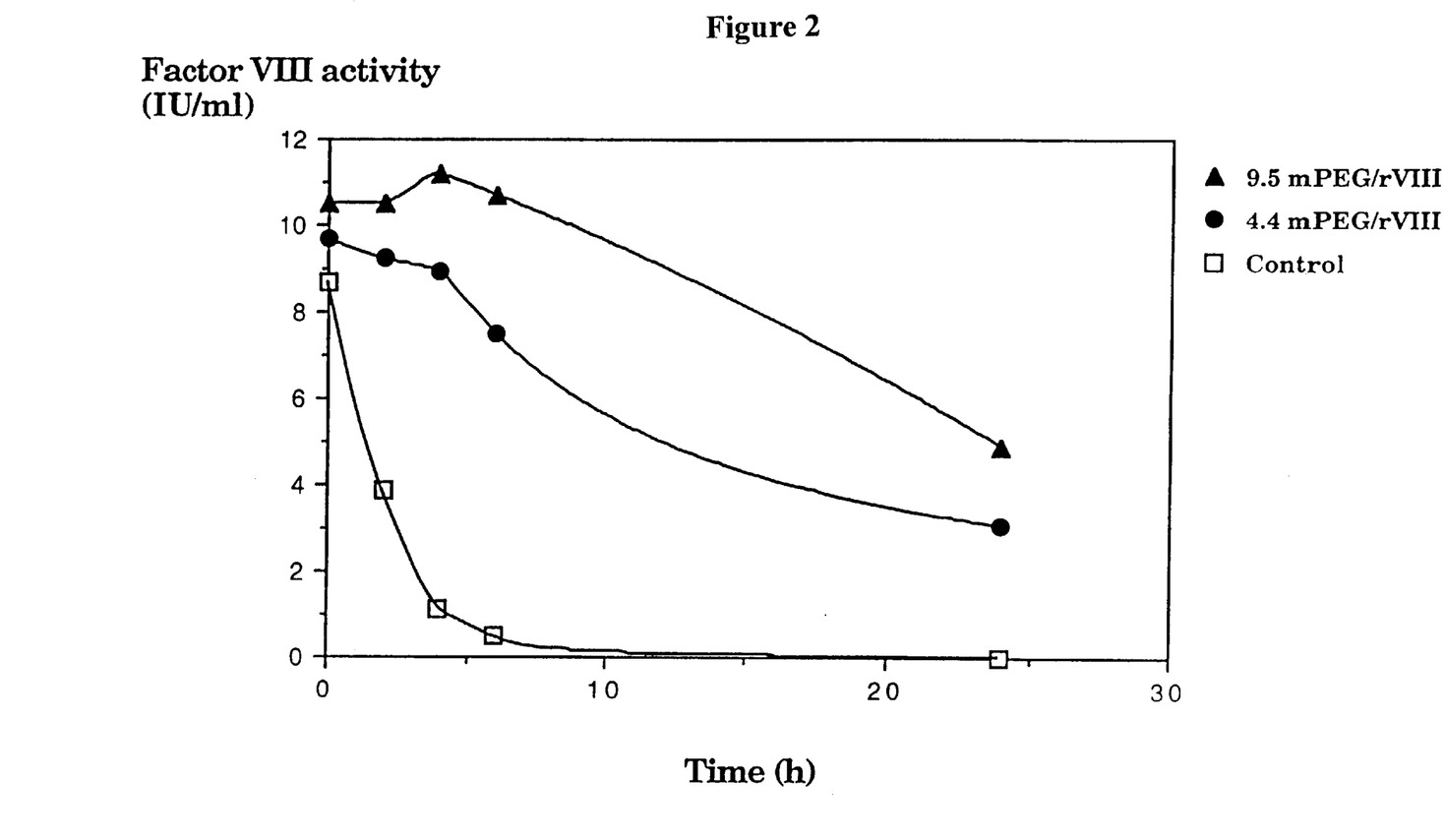
FIG. 2 set forth the Factor VIII activity, in IU/ml, as a function of time as obtained in the procedure described in Example 7.

The results in Table V and FIG. 2 show clearly that mPEG conjugation significantly enhanced the stability of factor VIII.

Example 8

Bioavailability Study of mPEGylated Factor VIII in Cynomolgus Monkeys

To evaluate the influence of the mPEG conjugation on the in-vivo stability of factor VIII a pharmacokinetic study was performed. Two preparations of mPEG conjugated factor VIII were produced as described in Example 3 and their specific activities were determined, as indicated in Table VI. To achieve high homogeneity of the derivatized material produced by the coupling procedure, fractionation of each preparation was performed twice by gel-permeation chromatography. A Superdex 200 PG XK 16/60 column (marketed by Pharmacia Biotech of Uppsala, Sweden) equilibrated with 19 mM L-histidine, 0.31 M NaCl, 3.4 mM $CaCl_2$, 0.02% Tween 80, pH 7.0 was used. Volume reduction of the factor VIII solutions prior to the second gel-permeation chromatography was performed in autoclaved Centriplus 30 concentrators; centrifugal ultrafiltration devices (cutoff 30 kDa, marketed by Amicon Inc. MA, USA). The solutions were concentrated three times at 2,500×g for 45 min. The pooled fractions obtained after the second gel-permeation chromatography were subsequently diluted in a buffer conforming to the final formulation; 19 mM L-Histidine, 0.31 M NaCl, 3.4 mM $CaCl_2$, 0.02% Tween 80, 17.5 mM sucrose, pH 7.0. The protein solutions were finally filtered using 0.22 μm Millex GV filters (marketed by Millipore, Mass., USA) and subsequently filled in autoclaved bottles. The solutions were stored at −70° C. until use. Six female cynomolgus monkeys were administered single intravenous doses of Preparation 1 of 250 IU/kg and single subcutaneous doses of Preparation 1 and Preparation 2 of 1,500 IU/kg at different occasions. All solutions were diluted 1:1 with water for injection before administration. The injection site for subcutaneous administration was in the left or the right dorsal region of the animal, and for intravenous administration in the left or the right cephalic veins respectively. Blood samples were collected from all animals via femoral vein puncture into tubes containing sodium citrate as anticoagulant (10% of the total volume) at the following durations after injection:

Intravenous administration: 0 (predose), 0.25, 1, 2, 4, 8, 24, 30, 48 h. Subcutaneous administration: 0 (predose), 3, 6, 9, 12, 15, 24, 30, 48 h. A pharmacokinetic study of non-conjugated factor VIII was performed in a separate study in the same species. The doses, route of administration and results (mean (±standard deviation (SD))) are shown in Table VI.

TABLE VI

| | Specific activity (IU/mg) | Route of administration | Doses (IU/kg) | Half-life (h) | Bioavailability (F[1]) (mean ± SD) |
|---|---|---|---|---|---|
| Non-conjugated r-VIII SQ | 15,000 | I.V. | 250 | 6.7 | — |
| mPEG - rVIII Preparation 1 | 10,000 | I.V. | 250 | 8.3 | — |
| Non-conjugated r-VIII SQ | 15,000 | S.C. | 2,500 | — | 0.053 (0.021) |
| mPEG - r VIII Preparation 1 | 10,000 | S.C. | 1,500 | — | 0.22 (0.13) |
| mPEG - r VIII Preparation 2 | 6,700 | S.C. | 1,500 | — | 0.19 (0.15) |

I.V. = intravenous
S.C. = subcutaneous
[1]F = AUC (S.C.) × DOSE (I.V.) / AUC (I.V.) × DOSE (S.C.)
wherein AUC is the area under the plasma concentration-time curve.

An evident from Table VI subcutaneous administration of both preparations of the mPEG conjugated factor VIII resulted in a markedly higher bio-availability compared subcutaneous administration of non-conjugated r-VIII SQ. Statistical analysis using the Student's t-test confirmed that the difference was significant.

We claim:

1. A process for improving the in vivo function of factor VIII by shielding exposed targets of the factor VIII, comprising a) immobilizing the factor VIII by interaction with a group-specific adsorbent carrying ligands manufactured by organic-chemical synthesis, for preventing polymer coupling to reactive amino acids of the immobilized factor VIII, within or adjacent to interaction domains;

b) activating a biocompatible polymer;

c) conjugating the activated biocompatible polymer to external sites of the immobilized factor VIII; and thereafter d) eluting the conjugate from the adsorbent.

2. A process according to claim 1, wherein the factor VIII is a deletion derivative of full-length factor VIII with coagulant activity.

3. A process according to claim 2, wherein the deletion derivative of factor VIII is deletion derivative recombinant factor VIII SQ (r-VIII SQ).

4. A process according to claim 1, wherein the specific activity of the factor VIII is at least 2,000 IU/mg of total protein prior to immobilization.

5. A process according to claim 4, wherein the specific activity of the factor VIII lies in the range of from 5,000 to 20,000 IU/mg of total protein prior to immobilization.

6. A process according to claim 1, wherein the activity of the factor VIII is at least 2,000 IU/ml prior to immobilization.

7. A process according to claim 6, wherein the activity of the factor VIII lies in the range of from 5,000 to 50,000 IU/ml prior to immobilization.

8. A process according to claim 1, wherein the biocompatible polymer is selected from the group consisting of homopolymers, copolymers and block copolymers of monoalkyl-capped polyalkyleneoxides.

9. A process according to claim 8, wherein the monoalkyl-capped polyalkyleneoxide is selected from the group consisting of polyethyleneglycol homopolymers and polypropyleneglycol homopolymers.

10. A process according to claim 9, wherein the monoalkyl-capped polyalkyleneoxide is a monomethoxy polyethyleneglycol (mPEG).

11. A process according to claim 1, wherein the ligands are selected from the group consisting of anionic or cationic exchange groups, sulfhydryl groups, immobilized metal affinity chromatography (IMAC) groups, straight or branched, saturated or unsaturated hydrocarbon chains and aromatic groups.

12. A process according to claim 11, wherein the anionic exchange groups are selected from the group consisting of quaternary aminomethyl, quaternary aminoethyl and trimethylaminoethyl, and mixtures thereof.

13. A process according to claim 1, wherein the biocompatible polymer is conjugated by covalent binding carried out on amino groups of the factor VIII by reagents selected from the group consisting of activated monoalkyl-capped polyalkylene oxide.

14. A process according to claim 13, wherein the activated monoalkyl-capped polyalkylene oxide is selected from the group consisting of mPEG-tresylate and a mixed anhydride of mPEG-succinate.

15. A conjugate of deletion derivative recombinant factor VIII SQ (r-VIII SQ) and a biocompatible polymer obtained by the process according to claim 1, wherein the degree of conjugation lies in the range of from 2 to 15 monoalkyl-capped PEG/r-VIII SQ molecule.

16. Method for treatment of hemophilia A, comprising subcutaneous, intramuscular, intradermal or intravenous administration of the conjugate of factor VIII and a biocompatible polymer according to claim 15.

17. A process according to claim 13, wherein the activated monoalkyl-capped polyalkylene oxide comprises activated monomethoxy polyethylene glycol.

18. A process for administering factor VIII, comprising subcutaneously, intramuscularly, or intradermally administering a conjugate of factor VIII and a biocompatible polymer eluted from an adsorbent on which is formed a conjugate of the biocompatible polymer and immobilized factor VIII, the factor VIII being immobilized by interaction with group-specific ligands manufactured by organic-chemical synthesis on the adsorbent, for preventing polymer coupling to reactive amino acids of the immobilized factor VIII, within or adjacent to interaction domains.

19. A process for administering factor VIII, comprising intravenously administering a conjugate of factor VIII and a biocompatible polymer eluted from an adsorbent on which is formed a conjugate of the biocompatible polymer and immobilized factor VIII, the factor VIII being immobilized by interaction with group-specific ligands manufactured by organic-chemical synthesis on the adsorbent, for preventing polymer coupling to reactive amino acids of the immobilized factor VIII, within or adjacent to interaction domains.

20. Method for treatment of hemophilia A, comprising subcutaneous, intramuscular, intradermal or intravenous administration of a conjugate of factor VIII and a biocompatible polymer eluted from an adsorbent on which is formed a conjugate of the biocompatible polymer and immobilized factor VIII, the factor VIII being immobilized by interaction with group-specific ligands manufactured by organic-chemical synthesis on the adsorbent, for preventing polymer coupling to reactive amino acids of the immobilized factor VIII, within or adjacent to interaction domains.

* * * * *